(12) United States Patent
Scarpaci et al.

(10) Patent No.: US 10,031,069 B2
(45) Date of Patent: *Jul. 24, 2018

(54) APPARATUS AND METHODS FOR CONCENTRATION DETERMINATION USING POLARIZED LIGHT

(71) Applicant: DEKA Products Limited Partnership, Manchester, NH (US)

(72) Inventors: Jacob W. Scarpaci, Manchester, NH (US); Jason M. Sachs, Chandler, AZ (US); Simon C. Helmore, Cambridge, MA (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/619,837

(22) Filed: Jun. 12, 2017

(65) Prior Publication Data

US 2017/0276596 A1 Sep. 28, 2017

Related U.S. Application Data

(63) Continuation of application No. 15/095,724, filed on Apr. 11, 2016, now Pat. No. 9,677,997, which is a
(Continued)

(51) Int. Cl.
*G01N 21/21* (2006.01)
*A61M 1/14* (2006.01)
(Continued)

(52) U.S. Cl.
CPC .............. *G01N 21/21* (2013.01); *A61M 1/14* (2013.01); *G01J 4/04* (2013.01); *G01N 21/90* (2013.01);
(Continued)

(58) Field of Classification Search
CPC .... G01J 4/00; G01J 4/04; G01J 21/21; G01N 21/21
(Continued)

(56) References Cited

U.S. PATENT DOCUMENTS 7,751,043 B2 * 7/2010 Scarpaci .................. G01J 4/04
356/364
8,432,547 B2 * 4/2013 Scarpaci .................. G01J 4/04
356/364
(Continued)

*Primary Examiner* — Roy M Punnoose
(74) *Attorney, Agent, or Firm* — Michelle Saquet Temple

(57) ABSTRACT

Methods and apparatus for concentration determination using polarized light. The apparatus includes a first polarized light source having a first light source polarization axis and a second polarized light source having a second light source polarization axis generally perpendicular to the first light source polarization axis. Also, a first polarized light receiver having a first polarized light receiver polarization axis and configured to measure an intensity of light transmitted from the first light receiver polarizer and a second polarized light receiver having a second polarized light receiver polarization axis substantially perpendicular to the first light receiver polarization axis and configured to measure an intensity of light transmitted from the second light receiver polarizer, wherein the first and second light receiver polarization axes are generally +/−45 degrees relative to the first and second light source polarization axes.

17 Claims, 13 Drawing Sheets

Related U.S. Application Data continuation of application No. 14/617,303, filed on Feb. 9, 2015, now Pat. No. 9,310,314, which is a continuation of application No. 13/872,399, filed on Apr. 29, 2013, now Pat. No. 8,953,162, which is a continuation of application No. 12/829,616, filed on Jul. 2, 2010, now Pat. No. 8,432,547, which is a continuation of application No. 12/263,927, filed on Nov. 3, 2008, now Pat. No. 7,751,043.

(60) Provisional application No. 60/985,003, filed on Nov. 2, 2007.

(51) Int. Cl.
*G01N 21/90* (2006.01)
*G01J 4/04* (2006.01)

(52) U.S. Cl.
CPC ............... *G01N 2201/0612* (2013.01); *G01N 2201/0683* (2013.01)

(58) Field of Classification Search
USPC ........................................................ 356/364
See application file for complete search history.

(56) References Cited

U.S. PATENT DOCUMENTS

| | | | |
|---|---|---|---|
| 8,953,162 B2 * | 2/2015 | Scarpaci ................... | G01J 4/04 356/364 |
| 9,310,314 B2 * | 4/2016 | Scarpaci ................... | G01J 4/04 |
| 9,677,997 B2 * | 6/2017 | Scarpaci ................... | G01J 4/04 |

* cited by examiner

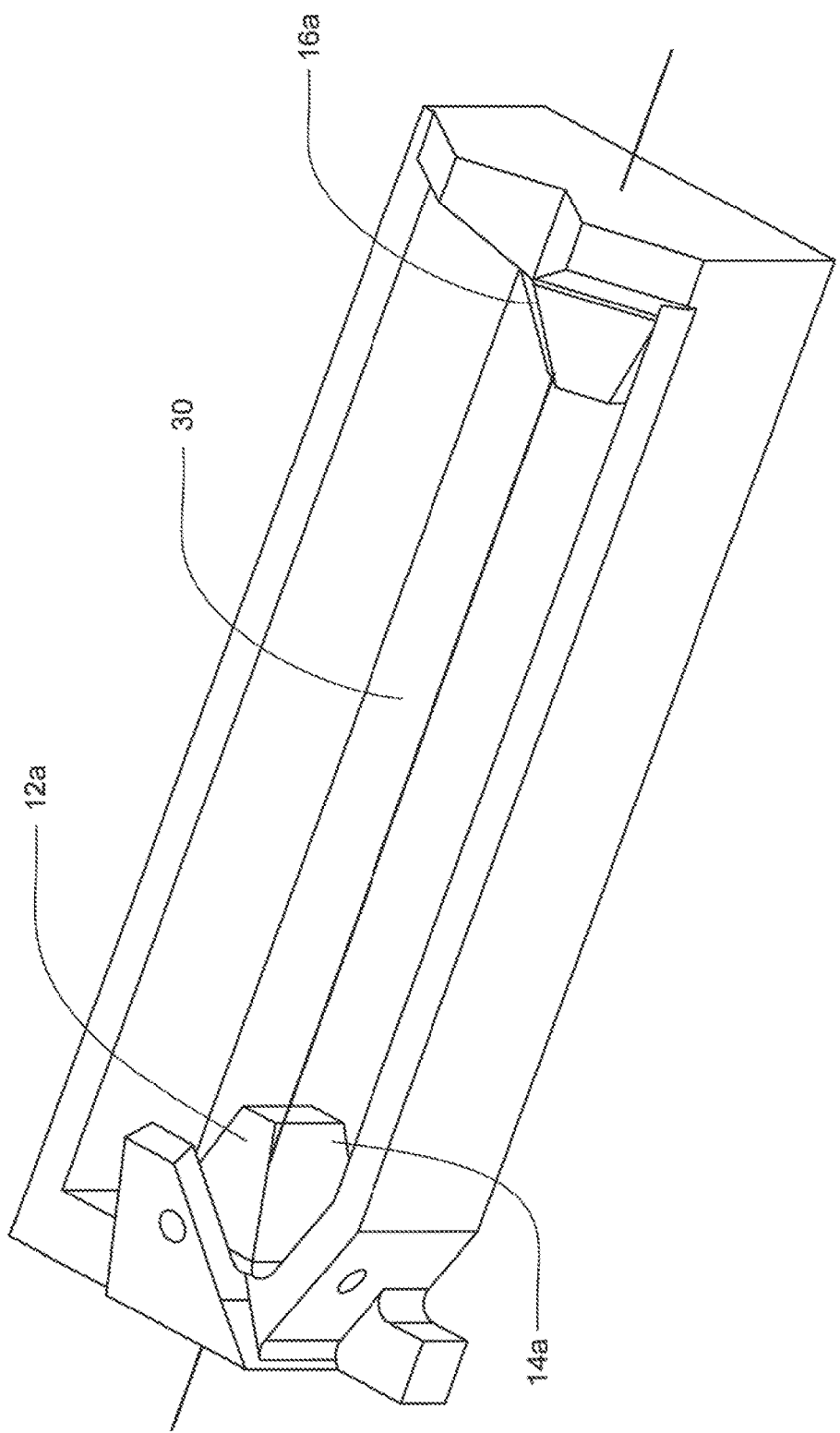

APPARATUS AND METHODS FOR CONCENTRATION DETERMINATION USING POLARIZED LIGHT

CROSS-REFERENCE TO RELATED APPLICATIONS

The present application is a Continuation application of prior U.S. patent application Ser. No. 15/095,724, filed Apr. 11, 2016, and entitled Apparatus and Methods for Concentration Determination Using Polarized Light, now U.S. Pat. No. 9,677,997, Issued Jun. 13, 2017, which is a Continuation application of prior U.S. patent application Ser. No. 14/617, 303, filed Feb. 9, 2015, and entitled Apparatus and Methods for Concentration Determination Using Polarized Light, now U.S. Pat. No. 9,310,314, Issued Apr. 12, 2016, which is a Continuation application of prior U.S. patent application Ser. No. 13/872,399, filed Apr. 29, 2013, and entitled Apparatus and Methods for Concentration Determination Using Polarized Light, now U.S. Pat. No. 8,953,162, Issued Feb. 10, 2015, which is a Continuation application of prior U.S. patent application Ser. No. 12/829,616, filed Jul. 2, 2010, and entitled Apparatus and Methods for Concentration Determination Using Polarized Light, now U.S. Pat. No. 8,432,547, Issued Apr. 30, 2013, which is a Continuation application of prior U.S. patent application Ser. No. 12/263, 927, filed Nov. 3, 2008, and entitled Apparatus and Methods for Concentration Determination Using Polarized Light, now U.S. Pat. No. 7,751,043, Issued Jul. 6, 2010, which claims the benefit of U.S. Provisional Application Ser. No. 60/985,003, filed Nov. 2, 2007, and entitled Quad Matrix Polarimeter, each of which is hereby incorporated herein by reference in its entirety.

FIELD OF THE INVENTION

The present disclosure relates to determining concentration of chiral molecules in a fluid, and more particularly to an apparatus and method for determining concentration of chiral molecules in a fluid using polarized light.

BACKGROUND ART

There are multiple reasons to detect the concentration of a compound in a solution. One reason for detecting concentration may be to ensure proper mixing of multi-component solutions. In order to increase the shelf life of a solution, in some circumstances, the various components may, for example, be kept in different chambers of a multi-chamber solution bag. The seal between the two chambers is then broken, mixing the various components. The concentration of the mixed solution can be used as an indicator to ensure that the chambers have been properly mixed.

Additionally, online mixing of two concentrations of a solution may be carried out to achieve a desired concentration. Automatically detecting the concentrations of solutions as well as creating and verifying a desired concentration, may allow for customized concentrations of solutions to be created, for example, without necessitating a premixed solution having the desired concentration. The ability to detect the available concentrations and to mix different concentrations may be used in a number of different applications.

In various additional circumstances, the concentration of glucose, a chiral molecule, in a solution, or determination of the mere presence of glucose may be desired.

SUMMARY OF THE INVENTION

According to one implementation, an apparatus includes a first polarized light source having a first light source polarization axis and a second polarized light source having a second light source polarization axis generally perpendicular to the first light source polarization axis. Also, a first polarized light receiver having a first polarized light receiver polarization axis and configured to measure an intensity of light transmitted from the first light receiver polarizer and a second polarized light receiver having a second polarized light receiver polarization axis substantially perpendicular to the first light receiver polarization axis and configured to measure an intensity of light transmitted from the second light receiver polarizer, wherein the first and second light receiver polarization axes are generally +/−45 degrees relative to the first and second light source polarization axes.

According to one implementation, an apparatus includes a first light source polarizer having a first light source polarization axis, and a second light source polarizer having a second light source polarization axis generally perpendicular to the first light source polarization axis. A first light receiver polarizer has a first light receiver polarization axis, and a second light receiver polarizer has a second light receiver polarization axis substantially perpendicular to the first light receiver polarization axis, wherein the first and second light receiver polarization axes are generally +/−45 degrees relative to the first and second light source polarization axes. A first light receiver is configured to measure an intensity of light transmitted from the first light receiver polarizer, and a second light receiver is configured to measure an intensity of light transmitted from the second light receiver polarizer.

One or more of the following features may be included. A first light source may be configured to provide light incident upon the first light source polarizer. The light incident upon the first light source polarizer may be substantially randomly polarized. A second light source may configured to provide light incident upon the second light source polarizer. The light incident upon the second light source polarizer may be substantially randomly polarized. One or more of the first light source and the second light source may include a laser diode.

A test region may be included, in which at least a portion of the test region may be at least partially disposed between the first and second light source polarizers and the first and second light receiver polarizers. The test region may include an at least partially transparent fluid passage configured to allow a fluid containing a concentration of chiral molecules to flow through the test region. The chiral molecules may include glucose molecules.

One or more of the first light source polarizer and the second light source polarizer may include an interface surface disposed at Brewster's angle relative to an optical path between at least one of the first light source polarizer and the second light source polarizer and at least one of the first light receiver polarizer and the second light receiver polarizer. One or more of the first light receiver polarizer and the second light receiver polarizer may include an interface surface disposed at Brewster's angle relative to an optical path between at least one of the first light source polarizer and the second light source polarizer and at least one of the first light receiver polarizer and the second light receiver polarizer.

According to another implementation, a method includes receiving light via a first optical path. The first optical path includes a first light source polarizer having a first light source polarization axis and a first light receiver polarizer having a first light receiver polarization axis being generally +45 degrees relative to the first light source polarization axis. Light is received via a second optical path. The second optical path includes the first light source polarizer and a second light receiver polarizer having a second light receiver polarization axis being generally −45 degrees relative to the first light source polarization axis. Light is received via a third optical path. The third optical path includes a second light source polarizer and the first light receiver polarizer. The second light source polarizer has a second light source polarization axis being generally 90 degrees relative to the first light source polarization axis. Light is received via a fourth optical path including the second light source polarizer and the second light receiver polarizer.

One or more of the following features may be included. Receiving light via the first and the second optical paths may include directing light from a first light source incident upon the first light source polarizer. The light from the first light source may be substantially randomly polarized. Receiving light via the third and the fourth optical paths may include directing light from a second light source incident upon the second light source polarizer. The light from the second light source may be substantially randomly polarized.

An intensity of light received via the first and third optical paths may be measured by a first light receiver. An intensity of light received via the second and fourth optical paths may be measured by a second light receiver. The first optical path, the second optical path, the third optical path, and the fourth optical path may include a test region. At least a portion of the test region may be at least partially disposed between the first and second light source polarizers and the first and second light receiver polarizers. The test region may include an at least partially transparent fluid passage that may be configured to allow a fluid containing a concentration of chiral molecules to flow through the test region. A polarization angle shift associated with the concentration of chiral molecules within the test region may be determined, based upon, at least in part, the respective intensity of light received via the first optical path, the second optical path, the third optical path, and the fourth optical path.

One or more of the first light source polarizer and the second light source polarizer may include an interface surface disposed at Brewster's angle relative to one or more of the first optical path, the second optical path, the third optical path, and the fourth optical path. One or more of the first light receiver polarizer and the second light receiver polarizer may include an interface surface disposed at Brewster's angle relative to one or more of the first optical path, the second optical path, the third optical path, and the fourth optical path.

The details of one or more implementations are set forth in the accompanying drawings and the description below. Other features and advantages will become apparent from the description, the drawings, and the claims.

BRIEF DESCRIPTION OF THE DRAWINGS

FIG. 5A diagrammatically depicts an embodiment of a quad matrix polarimeter assembly according to the embodiment shown in FIG. 5.

DETAILED DISCUSSION OF SPECIFIC EMBODIMENTS

Figure 1:
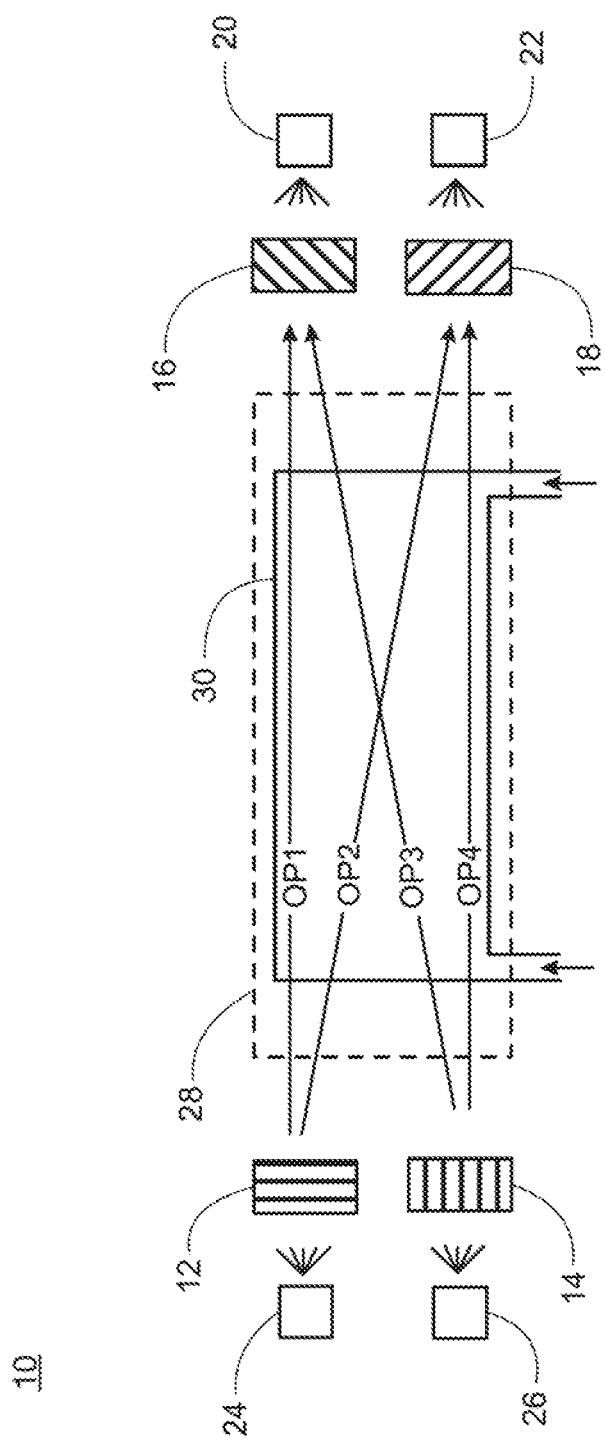
FIG. 1 schematically depicts an embodiment of a quad matrix polarimeter.

Referring to FIG. 1, quad matrix polarimeter 10 is schematically depicted. Quad matrix polarimeter 10 may generally include first light source polarizer 12 and second light source polarizer 14. First light source polarizer 12 may have a first light source polarization axis (e.g., which may be generally vertically oriented in the illustrated embodiment). Second light source polarizer 14 may have a second light source polarization axis that may be generally perpendicular to the first light source polarization axis (e.g., may be generally vertically oriented, in the illustrated embodiment).

Quad matrix polarimeter 10 may also include first light receiver polarizer 16 and second light receiver polarizer 18. Similar to first and second light source polarizers 12, 14, first light receiver polarizer 16 may have a first light receiver polarization axis and second light receiver polarizer 18 may have a second light receiver polarization axis that may be generally perpendicular to the first light receiver polarization axis. Further, the first and second light receiver polarization axes may be generally oriented at +/−45 degrees relative to the first and second light source polarization axes of first and second light source polarizers 12, 14. For example, in the illustrative embodiment of FIG. 1, the first and second light receiver polarization axes may be generally oriented at 45 degrees to the vertical (or horizontal), and may be generally perpendicular to one another. That is, the first light receiver polarization axis of first light receiver polarizer 16 may be oriented generally at 45 degrees to the right of vertical, and the second light receiver polarization axis of second light receiver polarizer 18 may be oriented generally at 45 degrees to the left of vertical.

Although FIG. 1 schematically represents embodiments having separate light source polarizers and light receiver polarizers, in some embodiments, the light source may be a polarized light source, i.e., a polarized light-emitting diode ("LED"), laser or other polarized light source, and the light receivers may be a receiver sensitive to light along one axis. In these embodiments, the light source polarizers and the light receiver polarizers would not be necessary and may be removed.

Consistent with the arrangement of the polarizers (e.g., first light source polarizer 12, and second light source polarizer 14 being generally perpendicular to one another and first light receiver polarizer 16 and second light source polarizer 18 being generally oriented at +/−45 degrees relative to first and second light source polarizers 12, 14), the relative polarizations may be as follows (in which first light source polarizer 12 is designated "A", second light source polarizer 14 is designated "B", first light receiver polarizer 16 is designated "C", and second light receiver polarizer 18 is designated "D"):

| Relative polarization between sources and sensors | | |
|---|---|---|
| source | sensor | relative polarization |
| A | C | $\theta_{AC} = \theta_{AC0} + \phi_{AC}$, where $\theta_{AC0} = 45°$ |
| A | D | $\theta_{AD} = \theta_{AD0} + \phi_{AD}$, where $\theta_{AD0} = -45°$ |
| B | C | $\theta_{BC} = \theta_{BC0} + \phi_{BC}$, where $\theta_{BC0} = -45°$ |
| B | D | $\theta_{BD} = \theta_{BD0} + \phi_{BD}$, where $\theta_{BD0} = 45°$ | where the angles $\theta_{xy0}$ are nominal angles and the angles $\phi_{xy}$ are manufacturing tolerance errors (e.g., $\phi_{AC} = \theta_C - \theta_A - \theta_{AC0}$, where $\theta_C$ and $\theta_A$ are the angles of each polarizer's axis of polarization, which may follow similarly for the other three pairs of polarizers) that have the relation $\phi_{AC} - \phi_{AD} - \phi_{BC} + \phi_{BD} = 0$. This can also be written as:

$$\phi_Q = \frac{\phi_{AD} + \phi_{BC}}{2} = \frac{\phi_{BD} + \phi_{AC}}{2} \quad (1)$$

which may be a characteristic quantity of the alignment of the polarizers.

Quad matrix polarimeter 10 may further include first light receiver 20 and second light receiver 22. First light receiver 20 may be configured to measure an intensity of light transmitted from first light receiver polarizer 16. Similarly, second light receiver 22 may be configured to measure an intensity of light transmitted from second light receiver polarizer 18. First and second light receivers 20, 22 may be any suitable light sensor that may measure the intensity of any light transmitted from first and second light receiver polarizers 16, 18, respectively. An example of a suitable light sensor may include, but is not limited to a TSL250RD sensor manufactured by TAOS Inc. of Plano Tex., which may be sensitive to wavelengths in the 300-1000 nm range with maximum responsivity at a wavelength of 750 nm and good responsivity (e.g., 50% of maximum) in the wavelength range of 450-900 nm. First and second light receivers 20, 22 may provide an output signal that is linearly proportional to the level of light intensity received, e.g., which may be digitized by an analog-to-digital converter. In some embodiments, light receivers 20, 22 may have a relatively fast response (e.g., less than about 10 milliseconds).

First and second light sources 24, 26 may be respectively associated with first and second light source polarizers 12, 14. First and second light sources 24, 26 may respectively provide light incident upon first and second light source polarizers 12, 14. The light from first and second light sources 24, 26, which may be incident upon respective first and second light source polarizers 12, 14, may be generally randomly polarized light. While any light source may generally be used (e.g., an incandescent light source, LED, etc.), according to an embodiment first and second light sources 24, 26 may include a collimated light source, such as a laser diode, a non-collimated light source in conjunction with one or more collimating optical elements (e.g., lenses, reflectors, etc.), or the like.

According to one aspect, quad matrix polarimeter 10 may be used to detect polarizing mediums and/or evaluate one or more characteristics of a polarizing medium. Accordingly, quad matrix polarimeter 10 may include test region 28, shown in broken line. At least a portion of test region 28 may be at least partially disposed between the light source polarizers (e.g., first light source polarizer 12 and second light source polarizer 14) and the light receiver polarizers (e.g., first light receiver polarizer 16 and second light receiver polarizer 18). As such, light passing from either of the light source polarizers (e.g., first light source polarizer 12 and/or second light source polarizer 14) to either light receiver polarizer (e.g., first light receiver polarizer 16 and/or second light receiver polarizer 18) may pass through test region 28.

Test region 28 may include fluid passage 30 configured to allow a fluid containing a concentration of chiral molecules (e.g., a polarizing medium) to flow through test region 28. Fluid passage 30 may be at least partially transparent, e.g., to light emitted by first and/or second light sources 24, 26. In one embodiment, fluid passage 30 may be a portion of a dialysis apparatus (e.g., may include a portion of a dialysis cassette through which a dialysate may flow). In an embodiment in which fluid passage 30 may include a portion of a dialysis apparatus, the fluid containing a concentration of chiral molecules may include a glucose solution, in which glucose may be the chiral molecule.

Figure 2:
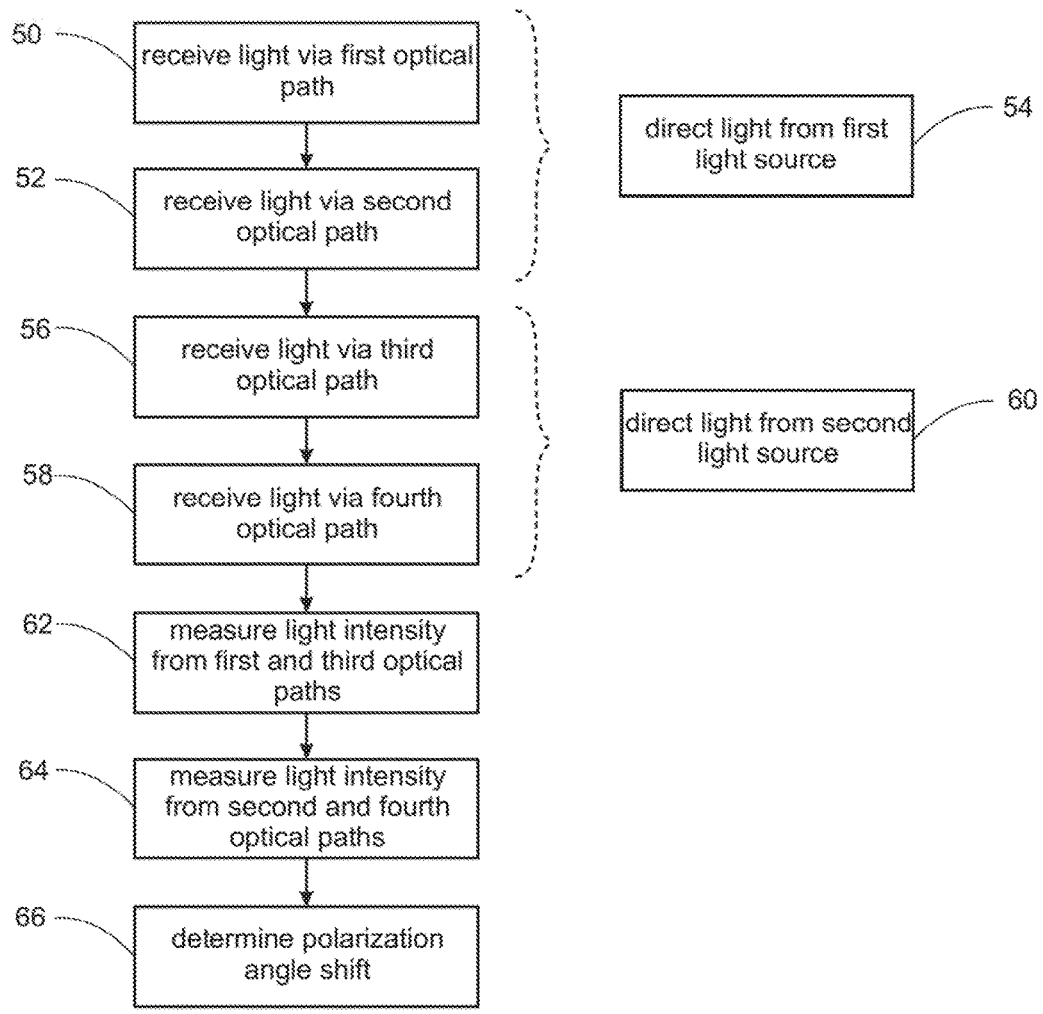
FIG. 2 is a flow chart of a polarization angle shift determination process that may be performed utilizing the quad matrix polarimeter of FIG. 1.

Referring also to FIG. 2, a method for determining the presence and/or character of a polarizing medium may include receiving 50 light via first optical path OP1, in FIG. 1. As shown in FIG. 1, first optical path OP1 may include first light source polarizer 12 and first light receiver polarizer 16. Additionally, light may be received 52 via second optical path OP2, in FIG. 1. Second optical path OP2 may include first light source polarizer 12 and second light receiver polarizer 18. Receiving light 50, 52 via first optical path OP1 and second optical path OP2 may include directing 54 substantially randomly polarized light from first light source 24 incident upon first light source polarizer 12.

Similarly, light may be received 56 via third optical path OP3, in FIG. 1. Third optical path OP3 may include second light source polarizer 14 and first light receiver polarizer 16. Additionally, light may be received 58 via fourth optical path OP4, in FIG. 1. Fourth optical path OP4 may include second light source polarizer 14 and second light receiver polarizer 18. Receiving 56, 58 light via third optical path OP3 and fourth optical path OP4 may include directing 60 substantially randomly polarized light from second light source 26 incident upon second light source polarizer 14.

An intensity of light received 50, 56 via the first and third optical paths (e.g., optical paths OP1 and OP3) may be measured 62 by first light receiver 20. Similarly, an intensity of light received 52, 58 via the second and fourth optical paths (e.g., optical paths OP2, OP4) may be measured 64 by second light receiver 22. As shown in the schematic diagram of quad matrix polarimeter 10 in FIG. 1, each of the optical paths (e.g., first optical path OP1, second optical path OP2, third optical path OP3, and fourth optical path OP4) may pass through test region 30 which may include a fluid containing a concentration of chiral molecules, such as a glucose solution, in one example. As will be appreciated, the chiral molecules (e.g., glucose) may act on the light transmitted from each of first light source polarizer 12 and second light source polarizer 14 causing a polarization angle shift of the light passing through the fluid containing the concentration of glucose.

Light transmitted from each of first light source polarizer 12 and second light source polarizer 14 may be incident upon both of first light receiver polarizer 16 and second light receiver polarizer 18 with sufficient intensity to produce an acceptable signal at both of first light receiver 20 and second light receiver 22. For example, if the path length of each of OP1, OP2, OP3, and OP4 is long enough relative to the distance between first light source polarizer 12 and second light source polarizer 14 and relative to the distance between first light receiver polarizer 16 and second light receiver polarizer 18, the light transmitted from each of first light source polarizer 12 and second light source polarizer 14 may be incident upon both the first light receiver polarizer 16 and the second light receiver polarizer 18.

While not shown, in the event that the length of the optical paths is not large enough relative to the separation between the light source polarizers and the light receiver polarizers to provide equivalent optical transfer functions among the optical paths (e.g., OP1, OP2, OP3 and OP4) one or more optical mergers and/or splitters may be utilized. For example, light from the two light sources may be joined together via an optical merger. Similarly, the joined light from the two light sources may be separated via an optical splitter that may be used to bring the light to the two light receivers. Examples of mergers/splitters may include, but are not limited to, a light pipe and an optical fiber bundle. Additionally, if optical mergers/splitters are employed, care may be taken to keep the polarization unchanged. For example, if an optical fiber bundle is used as an optical merger/splitter, the physical rotation of each fiber may be controlled in order to minimize/eliminate the effect of the polarization being changed in an unpredictable manner.

In an embodiment in which an optical merger/splitter is not used, the light sources may be positioned close enough to one another (although the intensity of light that travels from one light source through the polarizer associated with the other light source may be minimize, and similarly the light that travels to one light receiver through the polarizer associated with the other light receiver may also be minimized) that the axes between the light sources (e.g., including the light source polarizers) and the light receivers (including the light receiver polarizers) may be perpendicular to each other (e.g. the light sources mounted beside one another, and light receivers mounted above one another) to keep path length geometries as symmetric as possible between the four optical pathways.

The path length of the light transmitted through the glucose solution may vary according to design criteria and user need, as the path length may represent a compromise between attenuation of the light (as the path length increases) and an increase in the magnitude of polarization shift (as the path length increases). Regardless of the selected path length, it may be desirable that fluid passage 30 may not be a significant polarizer, or at least may exhibit spatially uniform polarization, such that the polarizing effect of fluid passage 30 may be separated from the polarization angle shift imparted by the glucose solution. Additionally, in the example of glucose as a chiral molecule, the light emitted by first and second light sources 24, 26 may have a wavelength of approximately 505 nm, in some embodiments, but in other embodiments, the wavelength used may vary depending on the receiver used. Glucose may exhibit a higher constant of polarization angle shift (also known as the "constant of optical rotation" or "specific rotation") at shorter wavelengths, which may increase the magnitude of polarization angle shift for a given path length. Thus, in various embodiments, it may be desirable to use the shortest wavelength that the system can transmit and receive.

A polarization angle shift associated with the concentration of chiral molecules within the test region may be determined 66, based upon, at least in part, the respective intensity of light received via first optical path OP1, second optical path OP2, third optical path OP3, and fourth optical path OP4 during an initial calibration and during data acquisition in the presence of the polarizing medium (e.g., the fluid including a concentration of chiral molecules). For example, quad matrix polarimeter 10 may be calibrated, e.g., by measuring 62, 64 the light intensity from each of the optical paths (e.g., OP1, OP2, OP3, and OP4) in the absences of a fluid including a concentration of chiral molecules. As such, the measured 62, 64 light intensity may be an intensity of the light experiencing only the polarizing effects of first and second light source polarizers 12, 14 and first and second light receiver polarizers 16, 18. The intensity of light from the respective optical paths (OP1, OP2, OP3, OP4) may also be measured 62, 64 when test region 28 includes the fluid including a concentration of chiral molecules.

The light sources (e.g., first light source 24 and second light source 26) may be turned on and off (e.g., by a microprocessor and/or other suitable controller) and the response of each light receiver (e.g., first light receiver 20 and second light receiver 22) may be measured, giving rise to four transfer functions that may reduce and/or eliminate the effect of ambient light. Two exemplary sampling schemes may include (wherein light transmitted via first light source 24 and first light source polarizer 12 is designated "A", light transmitted via second light source 26 and second light source polarizer 14 is designated "B", light received via first light receiver polarizer 16 and first light receiver 20 is designated "C", and light received via second light receiver polarizer 18 and second light receiver 22 is designated "D"):

| Sampling scheme 1 | |
|---|---|
| step | action |
| 1 | Turn off sources A and B. Wait for a predetermined settling time. Measure signal at sensors C and D, and call these $V_{OC}$ and $V_{OD}$ |
| 2 | Turn on source A and keep B off. Wait for a predetermined settling time. Measure signal at sensors C and D, and call these $V_{AC}$ and $V_{AD}$. |
| 3 | Turn on source B and turn A off. Wait for a predetermined settling time. Measure signal at sensors C and D, and call these $V_{BC}$ and $V_{BD}$. |

Transfer functions may then be derived from sampling scheme 1 as follows:

$$H_{AC} = V_{AC} - V_{OC}$$

$$H_{BC} = V_{BC} - V_{OC}$$

$$H_{AD} = V_{AD} - V_{OD}$$

$$H_{BD} = V_{BD} - V_{OD} \qquad (2)$$

| Sampling scheme 2 | |
|---|---|
| step | action |
| 1 | Turn off sources A and B. Wait for a predetermined settling time. Measure signal at sensors C and D, and call these $V_{OC}$ and $V_{OD}$ |
| 2 | Turn on source A and keep B off. Wait for a predetermined settling time. Measure signal at sensors C and D, and call these $V_{AC}$ and $V_{AD}$. |
| 3 | Turn on both sources. Wait for a predetermined settling |

-continued

Sampling scheme 2

| step | action |
|---|---|
|  | time. Measure signal at sensors C and D, and call these $V_{ABC}$ and $V_{ABD}$. |
| 4 | Turn off source A but keep source B on. Wait for a predetermined settling time. Measure signal at sensors C and D, and call these $V_{BC}$ and $V_{BD}$. |

Transfer functions may then be derived from sampling scheme 2 as follows:

$$H_{AC} = V_{ABC} - V_{BC} + V_{AC} - V_{0C}$$

$$H_{BC} = V_{ABC} - V_{AC} + V_{BC} - V_{0C}$$

$$H_{AD} = V_{ABD} - V_{BD} + V_{AD} - V_{0D}$$

$$H_{BD} = V_{ABD} - V_{AD} + V_{BD} - V_{0D} \quad (3)$$

Either sampling scheme (as well as various other sampling schemes which will be apparent to those having skill in the art) may be employed. Neglecting saturation effects, sampling scheme 2 may generally be more symmetrical and may be more likely to produce measurements with less noise for a given measurement than sampling scheme 1. However, the measurements $V_{ABC}$ and $V_{ABD}$ may have the largest magnitudes and may, therefore, require less light for the other measurements in order to avoid saturation.

Determining 66 the polarization angle shift imparted by the fluid including the concentration of chiral molecules may include, at least in part, comparing the measured 62, 64 light intensity during calibration of quad matrix polarimeter 10 to the measured 62, 64 light intensity when test region 28 includes the fluid including the concentration of chiral molecules. The magnitude of the polarization angle shift induced by the concentration of chiral molecules in the fluid may result in an increase and/or decrease in the measured 62, 64 light intensity via each of the optical paths (OP1, OP2, OP3, and OP4) compared to the measured 62, 64 intensity during calibration.

Generally the transfer function for two polarizers (e.g., polarizer "A" and polarizer "C") placed in front of each other with their polarization axes aligned (e.g., pointing in the same direction) may be (and wherein corresponding equations will be apparent for the various polarizers, i.e., "B" and "D"):

$$H_{AC} = G_A \alpha_A K_{AC} \alpha_C G_C / 2 \quad (4)$$

where $G_A$ and $G_C$ are the gains of a light source incident on polarizer A and of a light receiver receiving light via polarizer A and polarizer C, $K_{AC}$ is a relative intensity related to the geometric dependencies of polarizer A and polarizer C (e.g., source A may have a nonuniform luminous intensity that varies with angle, receiver C may have a responsivity that varies with angle, and there may be properties of the particular path between A and C that increases or decreases $K_{AC}$ e.g. reflection or refraction effects), and $\alpha_A$ and $\alpha_C$ are the attenuations of light waves aligned with the polarization axes of the polarizers (if the polarizers were ideal, these factors would be 1.0). The factor of ½ is due to the fact that approximately half the light's intensity is aligned with the polarizers' polarization axes which is let through, and half of the light's intensity is perpendicular to the polarizer's polarization axes, which is filtered out.

As the polarizers are rotated with respect to each other, the equation may be rewritten as:

$$H_{AC} = G_A \alpha_A K_{AC} \alpha_C G_C (\theta_C + \cos 2(\theta_C - \theta_A))/4 = G_A \alpha_A K_{AC} \alpha_C G_C \cos^2(\theta_C - \theta_A)/2 \quad (5)$$

where $\theta_C$ and $\theta_A$ are the physical angles of the two polarization axes. If $\theta_C = \theta_A$ or $\theta_C = \theta_A + 180°$, $H_{AC} = G_A \alpha_A K_{AC} \alpha_C G_C / 2$. If $\theta_C = \theta_A \pm 90°$, then $H_{AC} = 0$. While real (e.g., non-ideal) polarizers attenuate, but may not perfectly filter out light waves perpendicular to their axis of polarization, the foregoing equation may provide a workable approximation.

Figure 3:
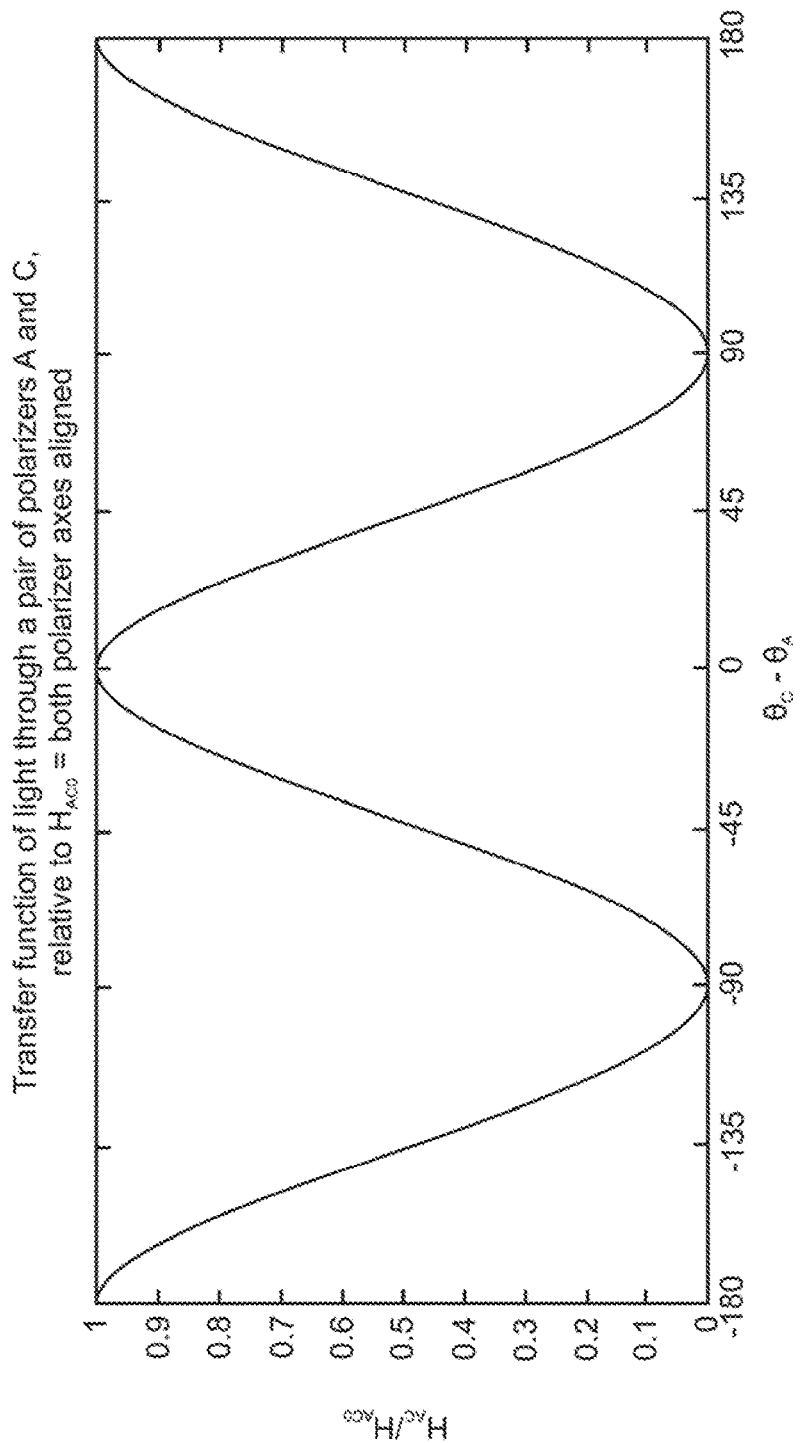
FIG. 3 is a graph representing the transfer function $H_{AC}$ as a function of θC−θA.

Referring also to FIG. 3, the transfer function $H_{AC}$, as a function of $\theta C - \theta A$, is shown. As shown in FIG. 3, the halfway-point for the transfer function is at ±45° (or the equivalent angles of ±135°; the effect of a polarizer may be invariant under a 180° rotation), which is approximately the point of steepest slope.

In the case of an isotropic (e.g., does not have a preferred orientation for light to pass, unlike polarizers that are highly anisotropic) polarization medium (e.g., in test region 28), the transfer function equation may be rewritten as:

$$H_{AC} = \frac{1}{4} G_A \alpha_A K_{AC} \alpha_M \alpha_C G_C (1 + \cos(2\theta_C - 2\theta_A + 2\theta_M)) \quad (6)$$
$$= G_{AC} R_{AC}(\theta_M)$$

where:

$$G_{AC} = \frac{1}{2} G_A \alpha_A K_{AC} \alpha_M \alpha_C G_C \quad (7)$$

$$R_{AC}(\theta_M) = \frac{1}{2}(1 + \cos(2\theta_{AC} + 2\theta_M))$$

and $\alpha_M$ is the medium's attenuation and $\theta_M$ is the polarization twist caused by the presence of chiral molecules. The function $R_{AC}(\theta_M)$ may be the same sine wave as shown in FIG. 3, but shifted left or right by twice the polarization twist $\theta_M$.

Referring to the transfer function vs. angle curve (e.g., as shown in FIG. 3) and the slope of the curve, it may be observed that the most sensitive orientation to small changes in polarization twist $\theta_M$ is when the two polarizers have their axes approximately 45° apart, and the least sensitive orientation to small changes in $\theta_M$ is when the polarizers are approximately parallel or perpendicular ($\theta_C - \theta_A = 0$ or ±90°).

In view of the foregoing, in the quad matrix (e.g., including the measured 62, 64 intensity of optical paths OP1, OP2, OP3 and OP4), if the relative polarization axes of the light source polarizers (e.g., first light source polarizer 12 and second light source polarizer 14) and of the light receiver polarizers (e.g., first light receiver polarizer 16 and second light receiver polarizer 18) are oriented as discussed above, then all four transfer functions (e.g., the transfer function corresponding to each optical path OP1, OP2, OP3, OP4) may operate at their most sensitive points to small changes in polarization twist $\theta_M$. For example, the two transfer functions (those dependent on $\theta_{AD}$ and $\theta_{BC}$, i.e., OP2 and OP3, which are nominally −45°) may increase with small positive $\theta_M$. In a related manner, the two transfer functions (those dependent on $\theta_{AC}$ and $\theta_{BD}$, i.e., OP1 and OP2, which are nominally 45°) may decrease with small positive $\theta_M$. The symmetry between the transfer functions may add enough redundancy of information so that if manufacturing tolerances cause some of the various gains to be unequal or the polarization axes are not quite 45° apart, the polarization twist $\theta_M$ may still be detected and may be insensitive to these manufacturing tolerances.

In view of the foregoing, determining 66 the polarization angle shift associated with the fluid including a concentration of chiral molecules may include measuring $H_{AC}$, $H_{BC}$, $H_{AD}$, $H_{BD}$ at time $T_0$ (i.e., when no fluid including a concentration of chiral molecules is present within test region 28) as a reference point. $H_{AC}$, $H_{BC}$, $H_{AD}$, $H_{BD}$ may also be measured at time $T_1$ (i.e., when the fluid including a concentration of chiral molecules is present within test region 28). Based upon, at least in part, the foregoing measurements of $H_{AC}$, $H_{BC}$, $H_{AD}$, $H_{BD}$ at $T_0$ and $T_1$, the following may be calculated:

$$\rho_{AC} = \frac{H_{AC}(T1)}{H_{AC}(T0)} \quad (8)$$

$$\rho_{AD} = \frac{H_{AD}(T1)}{H_{AD}(T0)}$$

$$\rho_{BC} = \frac{H_{BC}(T1)}{H_{BC}(T0)}$$

$$\rho_{BD} = \frac{H_{BD}(T1)}{H_{BD}(T0)}$$

If the system gains (e.g. light source intensity, receiver gain, attenuation, refraction/reflection effects) other than the test medium (i.e., fluid including a concentration of chiral molecules) attenuation do not change significantly between $T_0$ and $T_1$, then the $G_{AC}$ terms may cancel out, and we are left with:

$$\rho_{AC} = \alpha_M(T_1)/\alpha_M(T_0) \cdot R_{AC}(\theta_M(T_1))/R_{AC}(\theta_M(T_0)) = \quad (9)$$
$$\alpha_M(T_1)/\alpha_M(T_0) \cdot (1 + \cos2(\theta_C - \theta_A + \theta_M(T_1)))/$$
$$(1 + \cos2(\theta_C - \theta_A + \theta_M(T_0))).$$
$$\rho_{AC} = \rho_M \cdot (1 + \cos2(\theta_{AC0} + \phi_{AC} + \theta_M(T_1)))/$$
$$(1 + \cos2(\theta_{AC0} + \phi_{AC} + \theta_M(T_0)))$$

$$\rho_{AC} = \rho_M \frac{1 + \cos2(\theta_{AC0} + \phi_{AC} + \theta_M(T1))}{1 + \cos2(\theta_{AC0} + \phi_{AC} + \theta_M(T1))} \text{ where} \quad (10)$$

$$\rho_M = \alpha_M(T1)/\alpha_M(T0).$$

For $\theta_{AC0} = +45°$, this becomes:

$$\rho_{AC} = \rho_{AC} \cdot -\sin 2(\phi_{AC} + \theta_M(T_1)))/(1 - \sin 2(\phi_{AC} + \theta_M(T_0))).$$

$$\rho_{AC} = \rho_M \cdot (1 - \sin 2\phi_{AC} \cos 2\theta_M(T_1) - \cos 2\phi_{AC} \sin 2\theta_M(T_1))/(1 - \sin 2\phi_{AC} \cos 2\theta_M(T_0) - \cos 2\phi_{AC} \sin 2\theta_M(T_0))$$

If $\theta_{AC}$ and the $\theta_M$'s are small, then it may be shown that $$\rho_{AC} \approx \rho_M(1 - (1 + 2\phi_{AC})\sin 2\delta_M) \quad (11)$$

where $\delta_M = \theta_M(T_1) - \theta_M(T_0)$. \quad (12)

Similarly, $$\rho_{AD} \approx \rho_M(1 + (1 - 2\phi_{AD})\sin 2\delta_M) \quad (13)$$

$$\rho_{BC} \approx \rho_M(1 + (1 - 2\phi_{BC})\sin 2\delta_M) \quad (14)$$

$$\rho_{BD} \approx \rho_M(1 - (1 + 2\phi_{BD})\sin 2\delta_M) \quad (15)$$

Given the foregoing, it may be possible to compute the following four quantities which may help decorrelate some of the variables involved:

$$K_1 = \rho_{AC} + \rho_{AD} + \rho_{BC} + \rho_{BD} \quad (16)$$
$$\approx 4\rho_M - 2\rho_M \sin2\delta_M(\phi_{AC} + \phi_{AD} + \phi_{BC} + \phi_{BD}))$$
$$= 4\rho_M - 8\rho_M\phi_Q \sin2\delta_M$$

$$K_2 = -\rho_{AC} + \rho_{AD} + \rho_{BC} - \rho_{BD} \quad (17)$$
$$\approx 4\rho_M \sin2\delta_M + 2\sin2\delta_M(\phi_{AC} - \phi_{AD} - \phi_{BC} + \phi_{BD})$$
$$= 4\rho_M \sin2\delta_M$$

(since $\phi_{AC} - \phi_{AD} - \phi_{BC} + \phi_{BD} = 0$)

$$K_3 = \rho_{AC} + \rho_{AD} - \rho_{BC} - \rho_{BD} \quad (18)$$
$$\approx 2\rho_M \sin2\delta_M(-\phi_{AC} - \phi_{AD} + \phi_{BC} + \phi_{BD})$$
$$= 4\rho_M \phi_{BA} \sin2\delta_M$$

$$K_4 = \rho_{AC} - \rho_{AD} + \rho_{BC} - \rho_{BD} \quad (19)$$
$$\approx 2\rho_M \sin2\delta_M(-\phi_{AC} + \phi_{AD} - \phi_{BC} + \phi_{BD})$$
$$= 4\rho_M \phi_{CD} \sin2\delta_M$$

K3 and K4 are not used to calculate angle shift, but may rather represent additional degrees of freedom.

A basic estimate of angle shift may be derived from $K2/K1 \approx \sin 2\delta_M$, so:

$$\delta_{M1} = \frac{1}{2}\sin^{-1}\frac{K_2}{K_1} \approx \delta_M. \quad (20)$$

Empirical analysis seeking to correlate the various residual errors with known quantities, has shown that there are alternatives and improvements to the preceding estimator $\hat{\delta}_{M1}$.

For example, suppose we have a quad matrix:

$$M = \begin{bmatrix} M_{AC} & M_{AD} \\ M_{BC} & M_{BD} \end{bmatrix}$$

where $M_{ij}$ is some quantity relating source i to receiver j. (Examples are the gains and transfer functions $H_{ij}(T)$, $K_{ij}$, and $G_{ij}$ described above). Then define:

$$M_\chi = \frac{M_{AD}M_{BC}}{M_{AC}M_{BD}}$$

as a ratio of the two possible pair-wise products between sources and receivers. Thus:

$$H_\chi(T) = \frac{H_{AD}(T)H_{BC}(T)}{H_{AC}(T)H_{BD}(T)}. \quad (21)$$

An empirical relation may be derived such that:

$$\frac{1}{8}\ln H_\chi(T) \approx \sin(\theta_M(T) + \phi_Q) + \frac{5}{6}\sin^3(\theta_M(T) + \phi_Q) + \quad (22)$$
$$\frac{1}{8}\sin^2(\phi_{AC} - \phi_{BD}) + \frac{1}{8}\sin^2(\phi_{AD} - \phi_{BC}) + \frac{1}{8}\ln K_\chi \text{ where}$$

$$K_\chi = \frac{K_{AD}K_{BC}}{K_{AC}K_{BD}} \quad (23)$$

The empirical relation may relate the relative path-dependent gains which may be sensitive to reflection/refraction effects, and $\phi_Q$ (see equation 1) may relate the common-mode positioning error between the source/receiver polarizers (a change in $\phi_Q$ may not be able to be distinguished from a polarization shift of the test medium). The $\sin^2$ terms may be relatively small and may show dependence on the differential-mode positioning between the source and receive polarizers. The terms in equation 22 may be insensitive to changes in source/receiver gains and to any uniform attenuation that applies to all four transfer paths. By subtracting the resultant quantities at time $T_1$ from those at time $T_0$, the last three terms may cancel out and yield:

$$\hat{S}_{M2} = \frac{1}{8}\ln H_\chi(T1) - \frac{1}{8}\ln H_\chi(T0) \quad (24)$$

$$= \frac{1}{8}\ln\frac{H_\chi(T1)}{H_\chi(T0)}$$

$$\approx \sin(\theta_M(T1) + \phi_Q) + \frac{5}{6}\sin^3(\theta_M(T1) + \phi_Q) -$$

$$\sin(\theta_M(T0) + \phi_Q) + \frac{5}{6}\sin^3(\theta_M(T0) + \phi_Q)$$

$$\approx \sin\theta_M(T1) - \sin\theta_M(T0)$$

with estimators $$\hat{\delta}_{M2} = \hat{S}_{M2} = \delta_M \quad (25)$$

$$\hat{\delta}_{M2a} = \hat{S}_{M2}\left(1 - \frac{1}{6}\hat{S}_{M2}^2\right)$$

where the estimator $\hat{\delta}_{M2a}$ may reduce error slightly by compensating for the nonlinearity of equation 22, but not much when compared to unknown experimental sources of error (e.g. reflections or other nonlinearities).

The above estimators may be nearly equivalent to $\hat{\delta}_{M1}$ with similar accuracy and noise gain with respect to the transfer function measurements (Hij).

Additionally, it may be possible to reduce the error further by correlating the residual error of these estimators with terms dependent on the common-mode polarizer misalignment $\phi_Q$, or the terms K3 and K4 which may correlate with the differential modes of polarizer misalignment.

A third form of estimator has been derived empirically, and may be defined as follows. Let $$H_\gamma(T) = \frac{H_{AD}(T)H_{BC}(T) - H_{AC}(T)H_{BD}(T)}{H_{AC}(T)H_{AD}(T) + H_{AC}(T)H_{BC}(T) + H_{AC}(T)H_{BD}(T) +} \quad (26)$$
$$H_{AD}(T)H_{BD}(T)H_{BC}(T) + H_{BC}(T)H_{BD}(T)$$

$$= \frac{2(H_{AD}(T)H_{BC}(T) - H_{AC}(T)H_{BD}(T))}{(H_{AC}(T) + H_{AD}(T) + H_{BC}(T)H_{BD}(T))^2 -}$$
$$H_{AC}^2(T) - H_{BD}^2(T) - H_{AD}^2(T) - H_{BC}^2(T)$$

This equation can be used to form an estimator using the following equation:

$$\hat{S}_{M3} = \frac{3}{4}(H_\gamma(T1) - H_\gamma(T0)) \quad (27)$$

$$\hat{\delta}_{M3} = \hat{S}_{M3} \approx \delta_M.$$

This may not be quite as accurate as $\hat{\delta}_{M1}$ and $\hat{\delta}_{M2a}$ as it may be sensitive to differences in the source and receiver gains which may require compensation.

Consistent with the present disclosure, any suitable polarizer (such as a polarizing film) may be used for the first and second light source polarizers and the first and second light receiver polarizers. In addition to conventional polarizers, in some embodiments, a Pockels cell may be used, and in some embodiments, one or more liquid crystal display (LCD) units may be used as a polarizer. Liquid crystal displays may typically use twisted nematic liquid crystals to control the polarization angle shift in a liquid-crystal medium between 0° and 90° by application of an external voltage. The twisted nematic liquid crystals may be sandwiched between two polarizers. The resulting system may allow the display to then either transmit or block light.

A similar arrangement may be used in connection with an embodiment of quad matrix polarimeter, which may use a single light source and a single light receiver. A light source and a light source polarizer may be on one side of the test region. A light receiver polarizer and a light receiver may be on the other side of the test region. A twisted-nematic cell (an LCD without polarizers) or other optical rotator, that can be controlled to at least one of two polarization rotation states (e.g., 0° and 90°), may be used as the light source polarizer and/or the light receiver polarizer. The twisted-nematic cell light source polarizer and/or the twisted-nematic cell light receiver polarizer may be oriented with their optical axes 45° apart.

Consistent with the above configuration, the effective relative polarization of light between the light source polarizer and the light receiver polarizer may be $\theta_M \pm 45°$. Transfer functions $H_A$ and $H_B$ may be measured, one with the respective twisted-nematic cell polarizer at 0° and the other with the twisted-nematic cell polarizer at 90°. The two measurements may be repeated twice, first at time $T_0$ and then at time $T_1$. Ratios $\rho_A = H_A(T1)/H_A(T0)$ and $\rho_B = H_B(T1)/H_B(T0)$ may be calculated. The change in polarization angle of a polarizing medium in the test region between times $T_0$ and $T_1$ may be $$\text{be} \approx \frac{1}{2}\sin^{-1}\frac{\rho_B - \rho_A}{\rho_B + \rho_A},$$

which may be shown through similar reasoning as that given above.

In a similar manner, a single polarizer may be used for light source polarization and/or a single polarizer may be used for the light receiver polarizer. For example, the single polarizer may be rotated by 90° to achieve the light source polarization axis shift and/or the light receiver polarization axis shift. Similarly, an optical merger/splitter positioned between a single, stationary, polarizer and the test region (or between the light source and single polarizer or the single polarizer and the light receiver, on the other end of the test region) may be rotated to effect the polarization axis shift.

Figure 4:
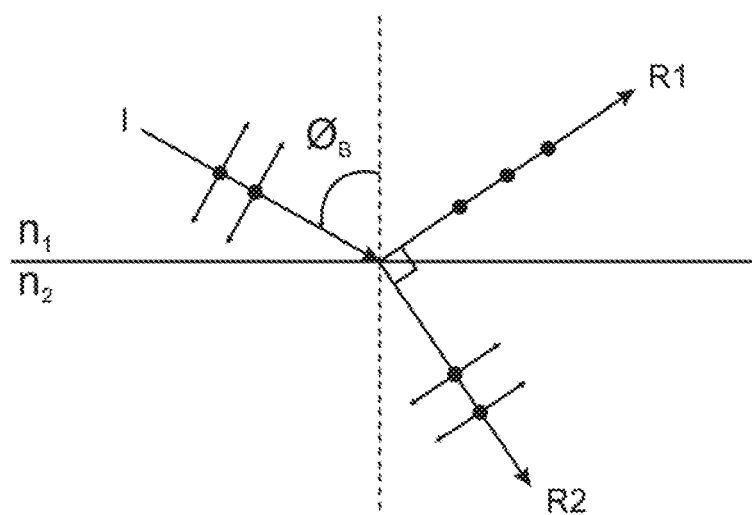
FIG. 4 diagrammatically depicts an optical path oriented at Brewster's angle relative to an interface surface.

Further, one or more of the first light source polarizer and the second light source polarizer may include an interface surface disposed at Brewster's angle relative to an optical path between at least one of the first light source polarizer and the second light source polarizer and at least one of the first light receiver polarizer and the second light receiver polarizer. Similarly, one or more of the first light receiver polarizer and the second light receiver polarizer may include an interface surface disposed at Brewster's angle relative to an optical path between at least one of the first light source polarizer and the second light source polarizer and at least one of the first light receiver polarizer and the second light receiver polarizer. Referring also to FIG. 4, Brewster's angle is the angle where reflected light (R1) and refracted light (R2) are at 90° relative to each other. The reflected light (R1) may be polarized parallel to the plane of reflection. The plane of reflection may be oriented to provide a desired plane of polarization.

The relative angles at which a beam of incident light (I) is reflected and refracted is dependent upon, at least in part, the refractive indices of the two mediums at the interface. Accordingly, Brewster's angle may be given by $\Theta_B = \tan^{-1}(n_2/n_1)$, where $n_1$ is the refractive index of the first medium and $n_2$ is the refractive index of the second medium forming the interface.

Figure 5:
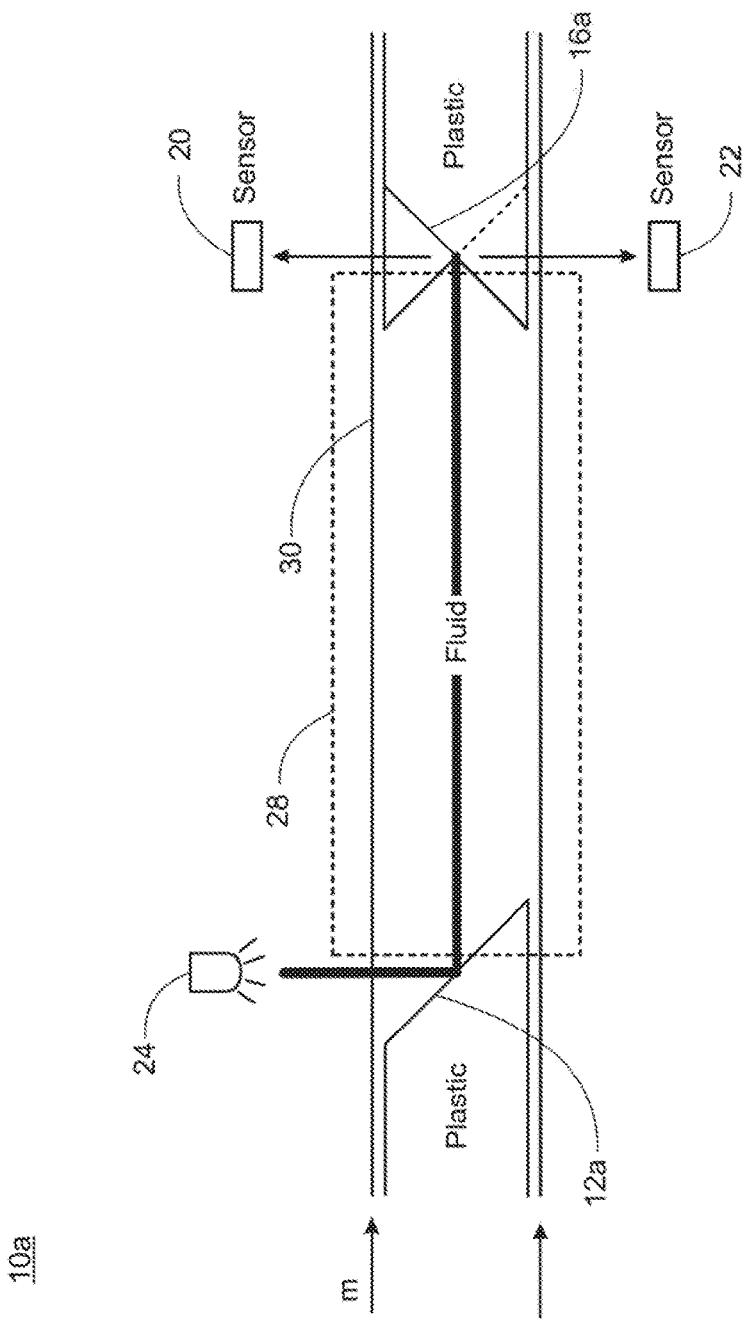
FIG. 5 schematically depicts an embodiment of a quad matrix polarimeter utilizing interface surfaces oriented at Brewster's angle as polarizing elements.
Figure 6:
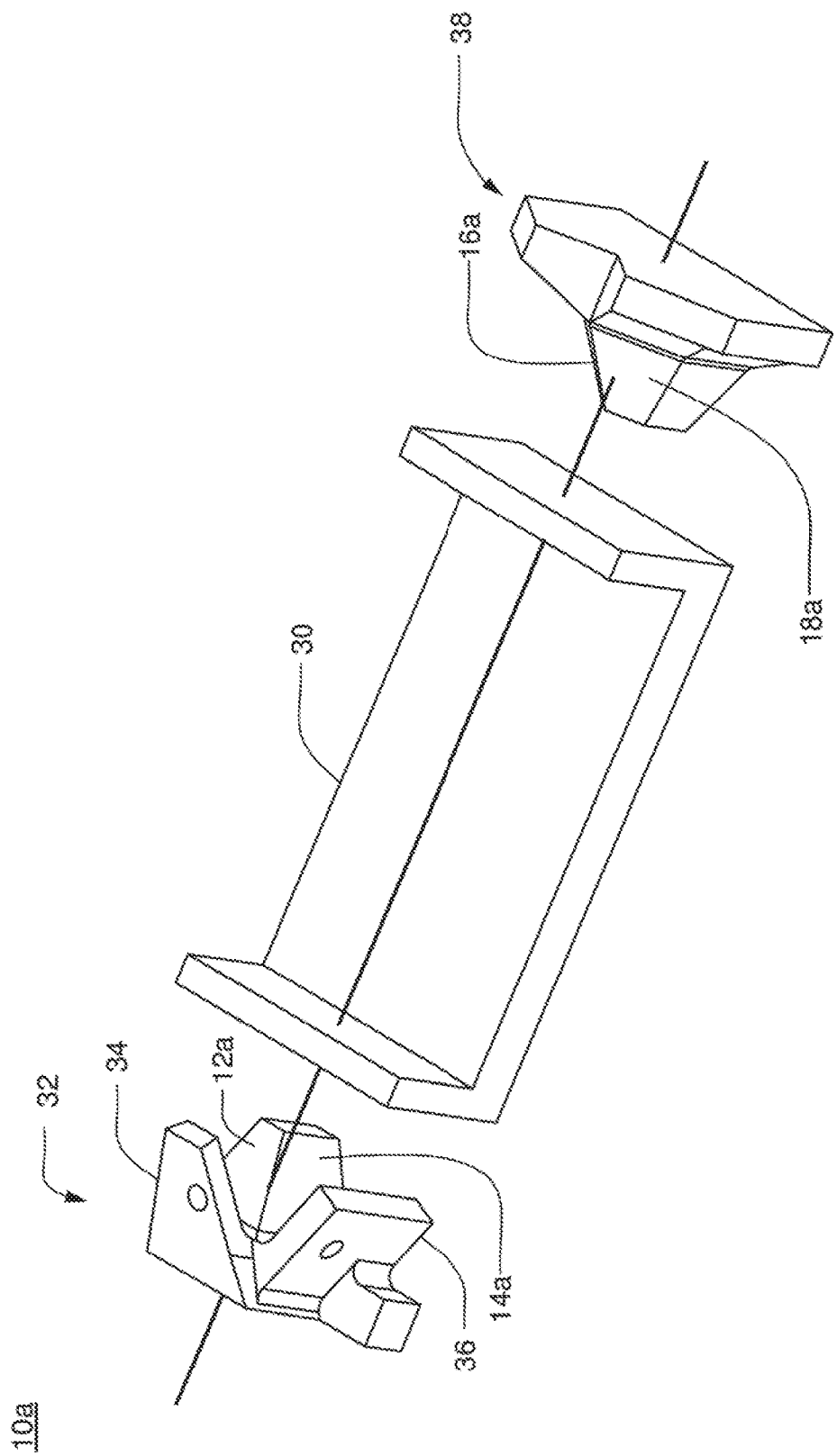
FIG. 6 diagrammatically depicts an exemplary embodiment of a quad matrix polarimeter.
Figure 7:
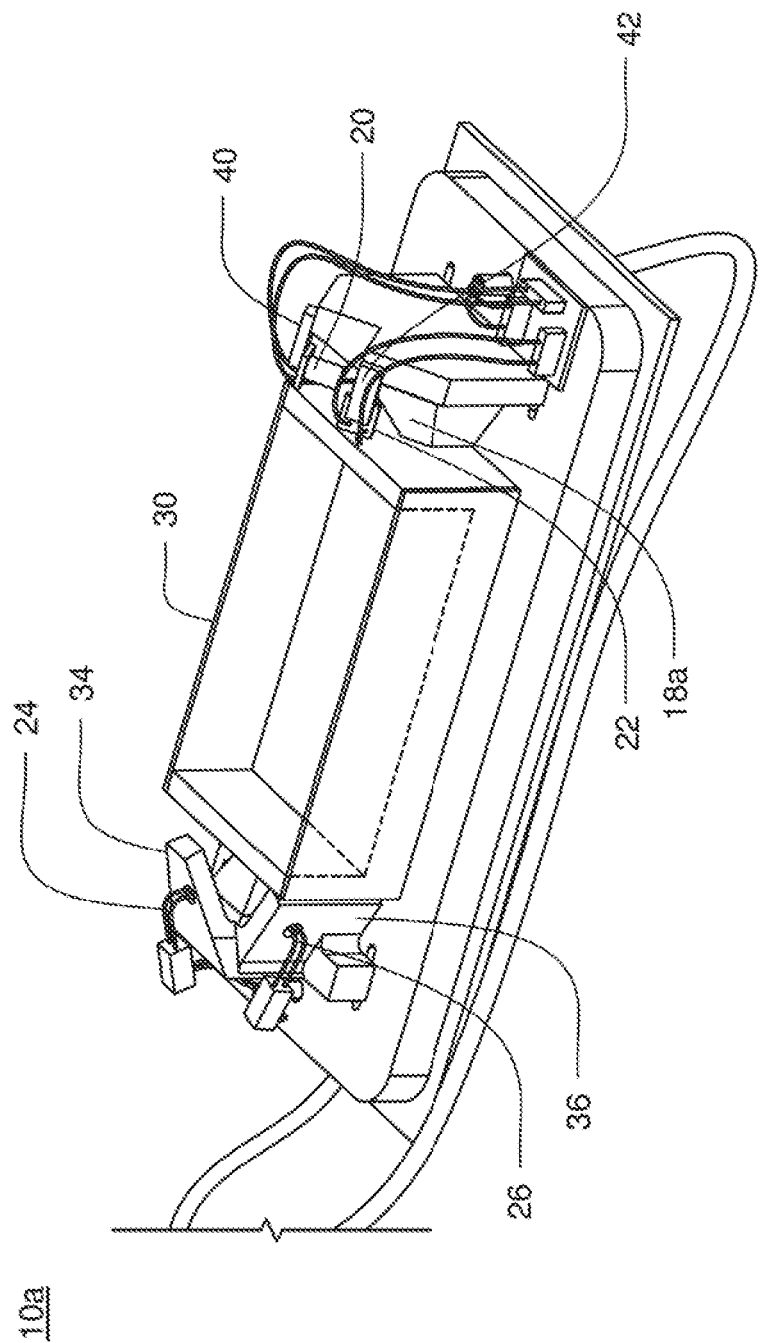
FIG. 7 diagrammatically depicts an embodiment of a quad matrix polarimeter assembly of FIG. 6.
Figure 8:
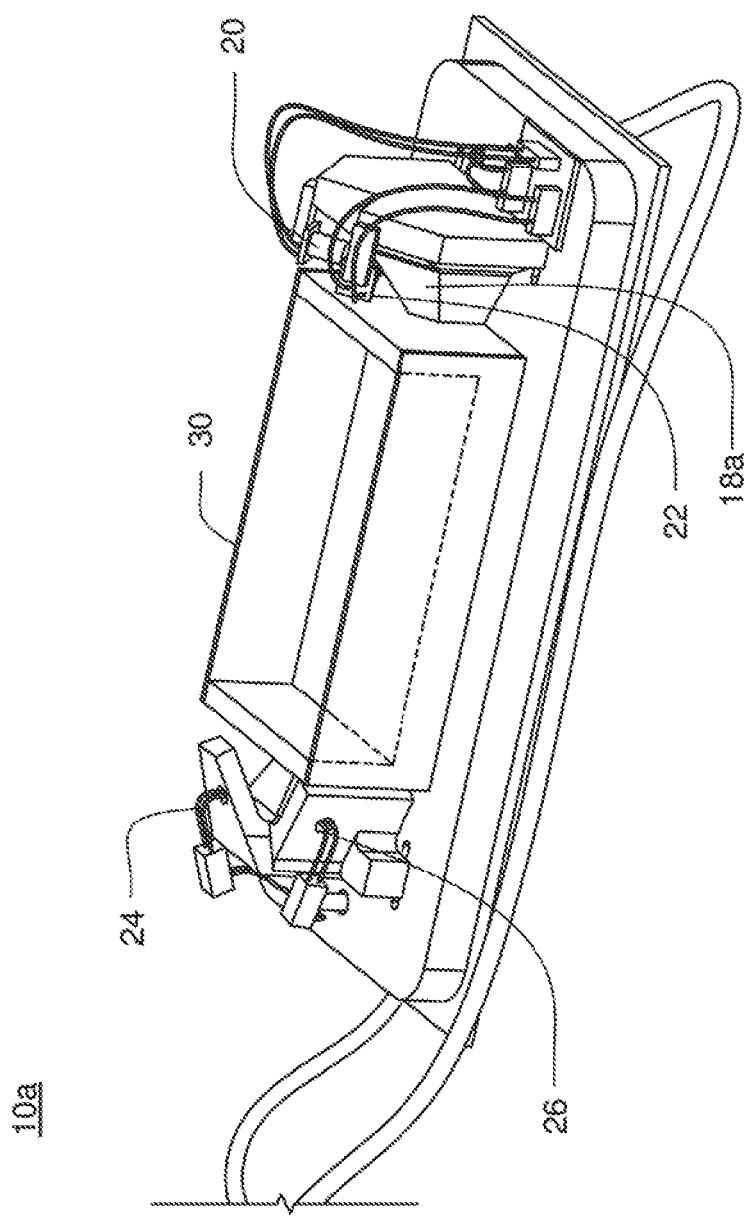
FIG. 8 diagrammatically depicts an embodiment of a quad matrix polarimeter assembly of FIG. 6.
Figure 9:
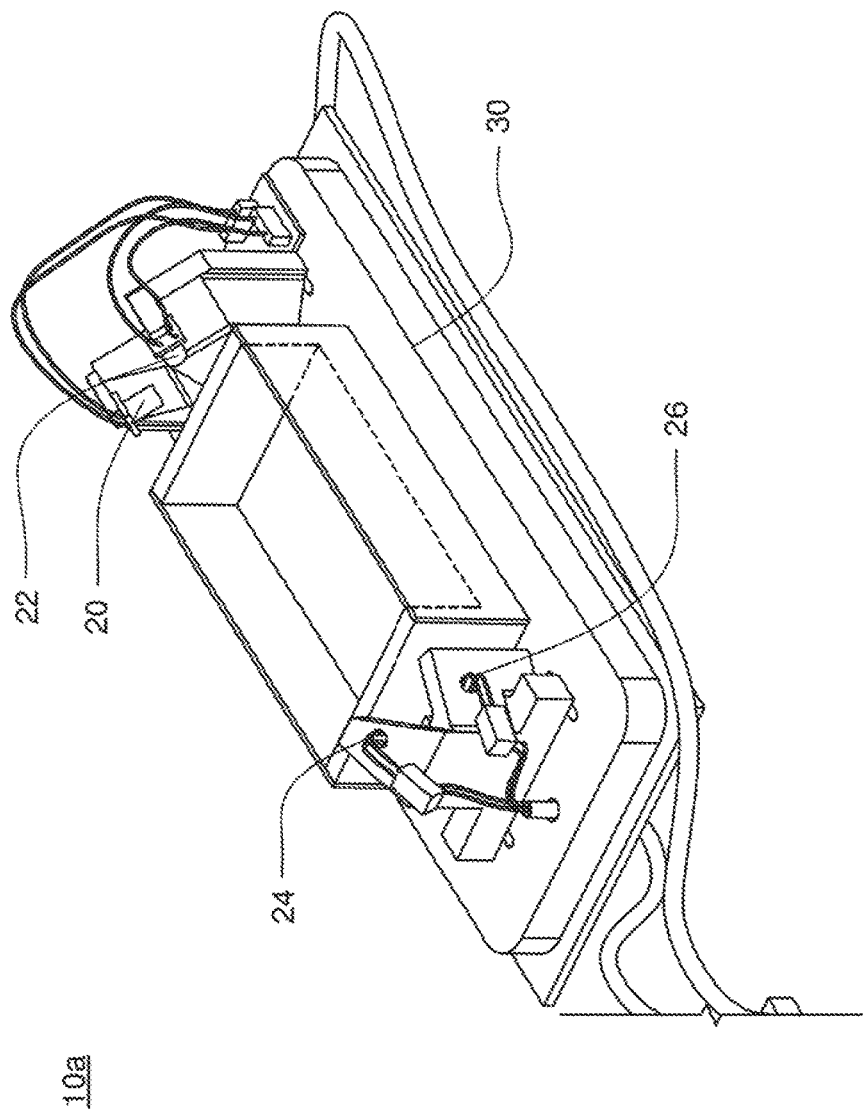
FIG. 9 diagrammatically depicts an embodiment of a quad matrix polarimeter assembly of FIG. 6.
Figure 10:
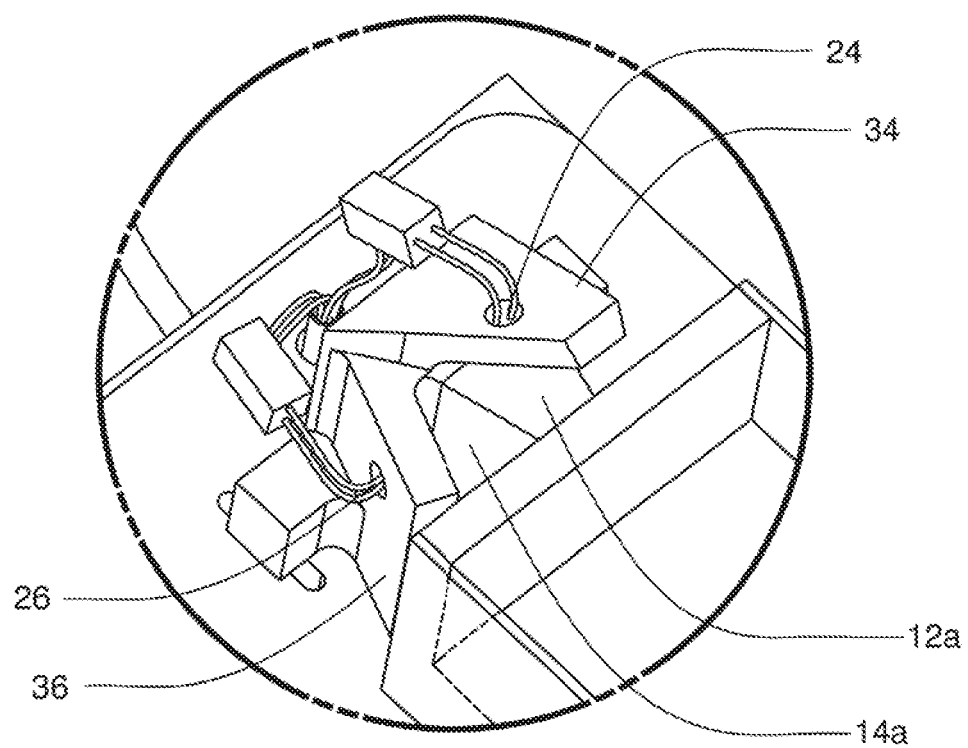
FIG. 10 is an enlarged view of a light source assembly of the embodiment of the quad matrix polarimeter assembly shown in FIG. 7-9.
Figure 11:
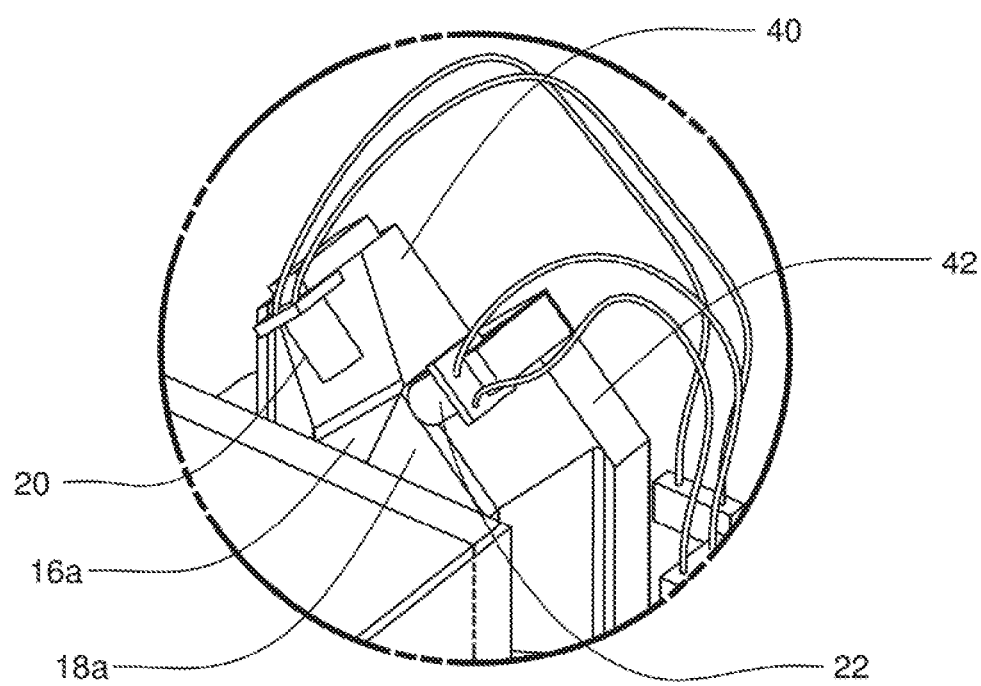
FIG. 11 is an enlarged view of a light receiver assembly of the embodiment of the quad matrix polarimeter assembly shown in FIG. 7-9.
Figure 12:
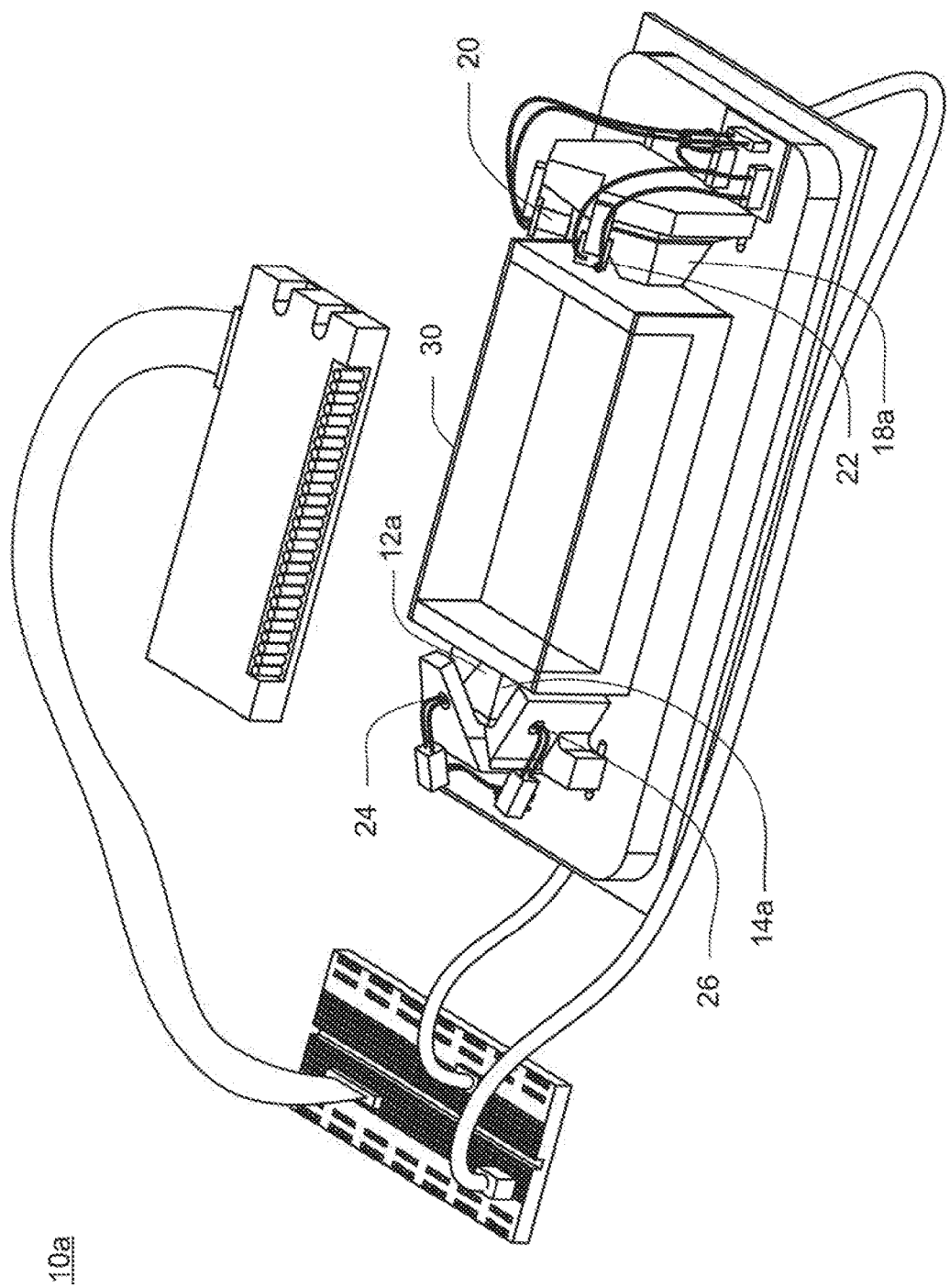
FIG. 12 diagrammatically depicts an embodiment of a quad matrix polarimeter assembly of FIG. 6.

Referring also to FIG. 5, an embodiment of quad matrix polarimeter 10a utilizing one or more at least partially reflective surfaces oriented at Brewster's angle as a light source polarizer (e.g., surface 12a) and as a light receiver polarizer (e.g., surface 16a) is diagrammatically shown. One embodiment of the apparatus is shown in FIG. 5A. In this embodiment, the Brewster's angle polarizers are molded into the fluid pathway such that the polarized light does not need to pass through anything other than the fluid under test. This embodiment may be desirable for it eliminates the probability of the polarized light angle being shifted upon passing through a surface before passing through the fluid under test.

In some embodiments, surfaces 12a, 16a may be oriented at Brewster's angle relative to the light path may allow light to be transmitted from a light source (e.g., light source 24) through one or more plastic components (e.g., membrane m, which may randomly polarize the light due to internal stresses in the plastic component), which may form at least a portion of fluid passage 30, and be polarized upon reflection by at least partially reflective surfaces 12a, 16a. As such, the random polarizing effect of the one or more plastic components may not be detrimental, and the need to provide a polarizer internal relative to the one or more plastic components may be avoided.

Referring also to FIGS. 6 through 12, an exemplary embodiment of quad matrix polarimeter 10a is shown. As shown, quad matrix polarimeter 10a may generally include at least partially reflective surfaces 12a, 14a oriented at Brewster's angle relative to an optical pathway through fluid passage 30. Surfaces 12a, 14a may be oriented generally perpendicular to one another, such that light (e.g., which may be provided by light sources 24, 26) reflected from surfaces 12a, 14a may be polarized with mutually perpendicular polarization axes. Similarly, quad matrix polarimeter 10a may include at least partially reflective surfaces 16a, 18a at an opposed end of fluid passage 30. Surfaces 16a, 18a may also be oriented at Brewster's angle relative to the optical pathway through fluid passage 30. As shown, surfaces 16a, 18a may be oriented generally perpendicular to one another, such that light (e.g., which may be transmitted from surfaces 12a, 14a) may be polarized with mutually perpendicular polarization axes. Additionally, surfaces 16a, 18a may be generally oriented at +/−45 degrees relative to surfaces 12a, 14a, such that the relative polarization angle of light transmitted from surfaces 12a, 14a and light transmitted from surfaces 16a, 18a to light receivers 20, 22 may be generally 45 degrees.

In one embodiment, surfaces 12a, 14a may be respective surfaces of an integrally molded component (e.g., component 32). Component 32 may include features 34, 36 for housing light sources 24, 26, respectively. Further, features 34, 36 may orient light sources 24, 26 in a desired orientation relative to surfaces 12a, 14a. Similarly, in one embodiment, surfaces 16a, 18a may be respective surfaces of an integrally molded component (e.g., component 38). Component 38 may include features 40, 42 for housing light receivers 20, 22. Further, features 34, 36 may orient light receivers 20, 22 in a desired orientation relative to surfaces 16a, 18a.

While the description herein-above has generally related to an apparatus utilizing two light source polarizers and two light receiver polarizers, other implementations are contemplated herein. For example, light source/light receiver polarizers at relative angles of ±45°, may work well for small values of test medium polarization angle shift $\theta_M$. If this angle is large, some of the approximations discussed above may become less accurate, and as $\theta_M$ approaches 45°, the ability to detect angle may become very poor because the transfer function curves may be at their minimum/maximum and have zero slope.

If it is desired to sense large polarization angles, one embodiment may include the use of one of the following setups:

1. 2 sources approximately 45° apart, 3 receivers approximately 120° apart
2. 3 sources approximately 120° apart, 2 receivers approximately 45° apart
3. 3 sources approximately 120° apart, 3 receivers approximately 120° apart
4. 2 sources (A and B) approximately 45° apart, 2 receivers (C and D) approximately 90° apart, with A and C approximately 90° apart, and B and D approximately 45° apart.
5. The same as the previous setup but with sources and receivers switched.

Each of the above alternatives may include the use of an appropriate set of optical mergers/splitters.

As will be discussed below, consistent the first two alternatives (two sources, three receivers or three sources, two receivers), having three sources or three receivers may allow the sensitivity to be good at all axes. The third alternative (three sources and three receivers) may not be necessary but may have some fault-tolerant advantages over the first two. The fourth and fifth alternatives may ensure that there may be at least two source-receiver transfer functions with nonzero slope $$\frac{dH_x}{d\theta_m},$$

but such a configuration may eliminate and/or reduce some of the self-compensating factors of the embodiment described above.

In an embodiment having three sources or three receivers, the sources may be A and B and the receivers may be C, D, and E. Transfer functions may be derived that are generally similar and/or identical in form to equations 6 and 7, namely $H_{ij} = G_{ij}(1 + \cos(2\theta_{ij} + 2\theta_m))$ where $G_{ij}$ is a fixed constant that is a function of geometry/optics/signal and receiver strength and $\theta_{ij}$ is the relative optical axis angle between corresponding polarizers. As such, $\cos(2\theta_{ij} + 2\theta_m) = K_c \cos 2(\theta_m + \theta_0) - K_s \sin 2(\theta_m + \theta_0)$ where $\theta_0$ represents a fixed angle offset between source A and receiver C that can be arbitrary, and $K_c = \cos 2(\theta_{ij} - \theta_m)$ and $K_s = \sin 2(\theta_{ij} - \theta_m)$.

| i (source) | j (receiver) | $\theta_{ij}$ | $K_c$ | $K_s$ |
|---|---|---|---|---|
| A | C | $\theta_0$ | 1 | 0 |
| A | D | $\theta_0 + 120°$ | −0.5 | −0.866 |
| A | E | $\theta_0 + 240°$ | −0.5 | 0.866 |
| B | C | $\theta_0 + 45°$ | 0 | 1 |
| B | D | $\theta_0 + 165°$ | 0.866 | −0.5 |
| B | E | $\theta_0 + 285°$ | −0.866 | −0.5 |

The goal for a large-signal angle decoder for $\theta_m$ may be to achieve two terms, one proportional to sin $(2\theta_m+2\theta_0)$ and the other to cos $(2\theta_m+2\theta_0)$, and then use a rectangular-to-polar conversion (or a 4-quadrant arctangent) to compute the angle $(2\theta_m+2\theta_0)$ from which $\theta_m$ may be determined (within a given 180° sector). A slight modification of the standard Clarke transform, as used in the field of motor control, may be used to convert the three receivers to two "virtual" receivers "x" and "y", for instance:

$$X_{Ax} = \frac{2}{3}X_{AC} - \frac{1}{3}X_{AD} - \frac{1}{3}X_{AE}$$

$$X_{Bx} = \frac{\sqrt{3}}{3}(X_{BD} - X_{BE})$$

$$X_{Ay} = \frac{\sqrt{3}}{3}(X_{AE} - X_{AD})$$

$$X_{By} = \frac{2}{3}X_{BC} - \frac{1}{3}X_{BD} - \frac{1}{3}X_{BE}$$

$X_{Ax}$ and $X_{Bx}$ may then be approximately proportional to sin $(2\theta_m+2\theta_0)$ and $X_{Ay}$ and $X_{By}$ may be approximately proportional to sin $(2\theta_m+2\theta_0)$. The "X", in the exemplary embodiments, may be a generic angle dependant function, or, in some embodiments, may be any generic quantity that may be roughly the optical transfer function, compensated for gain variation. This may be done either by calculating $X_{ij}=H_{ij}/G_{ij}$ where the system gain $G_{ij}$ may be determined at manufacturing time (but may be vulnerable to non-uniform gain drifts between sensor/receiver pairs), or $X_{ij}=\rho_{ij}=H_{ij}(T_1)/H_{ij}(T_0)$.

The fact that there may be redundancy in the light receiver (four transfer functions sensitive to changes in one quantity, or six in the case of some of the alternate embodiments) may mean that it may be possible to take a measure of the "health" of the light receiver outputs to be used as an indication of light receiver failure. It may additionally be possible to compensate for any determined failure. One example of a "health indicator" may be to use the quantities $K_1$ to $K_4$ (see equations 16-19), e.g. examine quantity $K_1$ which may stay fairly close to $4\rho_M$, despite angle shifts, or to compute the following empirically derived quantity:

$$F_{341} = \frac{K_3^2 + K_4^2}{K_2^2 + a}$$

The empirical number a may be used to prevent numerical overflow for $K_2$ near 0 which may happen when $\theta_m$ is small. Indicator $F_{341}$ may remain small and fairly constant as it may be strongly correlated to the relative angular positions between various pairs of polarizers.

A number of implementations have been described. Nevertheless, it will be understood that various modifications may be made. Accordingly, other implementations are within the scope of the following claims.

What is claimed is:

1. An apparatus comprising:
    a first polarized light source;
    a second polarized light source;
    a first polarized light receiver having a first polarized light receiver polarization axis and configured to measure an intensity of light transmitted from the first light receiver polarizer;
    a second polarized light receiver having a second polarized light receiver polarization axis substantially perpendicular to the first light receiver polarization axis and configured to measure an intensity of light transmitted from the second light receiver polarizer; and
    a test region, at least a portion of the test region at least partially disposed between the first and second light source polarizers and the first and second light receiver polarizers, wherein the test region comprising a fluid passage configured to allow a fluid containing a concentration of chiral molecules to flow through the test region, wherein the fluid passage located within a dialysis apparatus.

2. The apparatus of claim 1, wherein the first polarized light source having a first light source polarization axis.

3. The apparatus of claim 1, wherein the second polarized light source having a second light source polarization axis generally perpendicular to the first light source polarization axis.

4. The apparatus of claim 1, wherein the dialysis apparatus is a dialysis cassette.

5. The apparatus of claim 1, further comprising: an optical merger, wherein the optical merger merges the light from the first polarized light source and the second polarized light source.

6. The apparatus of claim 1 wherein the first and second light receiver polarization axes are generally +/−45 degrees relative to the first and second light source polarization axes.

7. An apparatus comprising:
    a first light source polarizer having a first light source polarization axis;
    a second light source polarizer having a second light source polarization axis generally perpendicular to the first light source polarization axis;
    a first light receiver polarizer having a first light receiver polarization axis;
    a first light receiver configured to measure an intensity of light transmitted from the first light receiver polarizer;
    a second light receiver polarizer having a second light receiver polarization axis substantially perpendicular to the first light receiver polarization axis;
    a second light receiver configured to measure an intensity of light transmitted from the second light receiver polarizer; and
    a test region, at least a portion of the test region at least partially disposed between the first and second light source polarizers and the first and second light receiver polarizers, wherein the test region comprising a fluid passage configured to allow a fluid containing a concentration of chiral molecules to flow through the test region wherein the fluid passage located within a dialysis apparatus.

8. The apparatus of claim 7, further comprising: an optical merger, wherein the optical merger merges the light from the first polarized light source and the second polarized light source.

9. The apparatus of claim 7, wherein the first and second light receiver polarization axes are generally +/−45 degrees relative to the first and second light source polarization axes.

10. The apparatus of claim 7, wherein the dialysis apparatus is a dialysis cassette.

11. The apparatus of claim 7, further comprising:
a first light source configured to provide light incident upon the first light source polarizer, the light incident upon the first light source polarizer being substantially randomly polarized; and
a second light source configured to provide light incident upon the second light source polarizer, the light incident upon the second light source polarizer being substantially randomly polarized.

12. The apparatus of claim 7, wherein one or more of the first light source and the second light source include a laser diode.

13. The apparatus of claim 7, further including a test region, at least a portion of the test region at least partially disposed between the first and second light source polarizers and the first and second light receiver polarizers.

14. The apparatus of claim 13, wherein the test region includes an at least partially transparent fluid passage configured to allow a fluid containing a concentration of chiral molecules to flow through the test region.

15. The apparatus of claim 14, wherein the chiral molecules include glucose molecules.

16. The apparatus of claim 7, wherein one or more of the first light source polarizer and the second light source polarizer comprise an interface surface disposed at Brewster's angle relative to an optical path between at least one of the first light source polarizer and the second light source polarizer and at least one of the first light receiver polarizer and the second light receiver polarizer.

17. The apparatus of claim 7, wherein one or more of the first light receiver polarizer and the second light receiver polarizer comprise an interface surface disposed at Brewster's angle relative to an optical path between at least one of the first light source polarizer and the second light source polarizer and at least one of the first light receiver polarizer and the second light receiver polarizer.

\* \* \* \* \*